(12) United States Patent
Schmied et al.

(10) Patent No.: US 11,540,812 B2
(45) Date of Patent: Jan. 3, 2023

(54) METHOD AND SYSTEM FOR INCREASING EFFECTIVE LINE DENSITY OF VOLUME COMPOUND ULTRASOUND IMAGES

(71) Applicant: General Electric Company, Schenectady, NY (US)

(72) Inventors: Heinz Schmied, Zipf (AT); Helmut Brandl, Zipf (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 696 days.

(21) Appl. No.: 16/229,590

(22) Filed: Dec. 21, 2018

(65) Prior Publication Data
US 2020/0196991 A1 Jun. 25, 2020

(51) Int. Cl.
*A61B 8/00* (2006.01)
*G01S 15/89* (2006.01)
*A61B 8/08* (2006.01)
*G01S 7/52* (2006.01)

(52) U.S. Cl.
CPC .......... *A61B 8/5253* (2013.01); *A61B 8/4494* (2013.01); *A61B 8/483* (2013.01); *A61B 8/5246* (2013.01); *G01S 7/52065* (2013.01); *G01S 7/52095* (2013.01); *G01S 15/8995* (2013.01); *G01S 15/8993* (2013.01)

(58) Field of Classification Search
CPC .......................................... A61B 8/5238–5253
See application file for complete search history.

(56) References Cited

U.S. PATENT DOCUMENTS

| | | | |
|---|---|---|---|
| 5,718,230 A | 2/1998 | Chapman et al. | |
| 6,530,885 B1* | 3/2003 | Entrekin | G01S 7/52053 128/916 |
| 6,733,453 B2 | 5/2004 | Freiburger et al. | |
| 2008/0154133 A1* | 6/2008 | Shiki | G01S 7/52095 600/443 |
| 2013/0012819 A1 | 1/2013 | Haugen et al. | |

(Continued)

OTHER PUBLICATIONS

Bradley et al., "Retrospective Transmit Beamformation" Siemens whitepaper, 2008 (Year: 2008).*

(Continued)

*Primary Examiner* — Colin T. Sakamoto
(74) *Attorney, Agent, or Firm* — McAndrews, Held & Malloy, Ltd.; Jacob Groethe; David Bates (57) ABSTRACT

Systems and methods for increasing effective line density of volume compound ultrasound images while maintaining the frame rate, penetration depth, and other image characteristics are provided. The method includes acquiring a first lateral plane at a first elevational position. The first lateral plane includes a first set of receive lines at a first set of lateral positions. The method includes acquiring a second lateral plane at a second elevational position adjacent the first elevational position. The second lateral plane includes a second set of receive lines at a second set of lateral positions laterally offset from the first set of lateral positions. The method includes combining the first lateral plane and the second lateral plane to generate a compound image and presenting the compound image at a display system. The compound image may be a volume compound image in an A-plane generated based on volume compound imaging rendering algorithms.

19 Claims, 6 Drawing Sheets

(56) References Cited

U.S. PATENT DOCUMENTS

2014/0066768 A1* 3/2014 Sui .................... G01S 7/52047
600/443
2015/0049578 A1 2/2015 Hoctor et al.

OTHER PUBLICATIONS

Schrope, Chapters. Advanced Technologies. In: Schrope B. eds. Surgical and Interventional Ultrasound. McGraw Hill; 2014. Accessed from https://accesssurgery.mhmedical.com/content.aspx?bookid=698&sectionid=45954783 (Year: 2014).*

Andresen, et al., "Rocking convex array used for 3D synthetic aperture focusing," http://ieeexplore.ieee.org/document/4803256, Mar. 21, 2009, 2008 IEEE Ultrasonics Symposium, 1 page.

* cited by examiner

METHOD AND SYSTEM FOR INCREASING EFFECTIVE LINE DENSITY OF VOLUME COMPOUND ULTRASOUND IMAGES

FIELD

Certain embodiments relate to ultrasound imaging. More specifically, certain embodiments relate to a method and system for increasing effective line density of volume compound ultrasound images while maintaining the frame rate, penetration depth, and other image characteristics.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Figure 1:
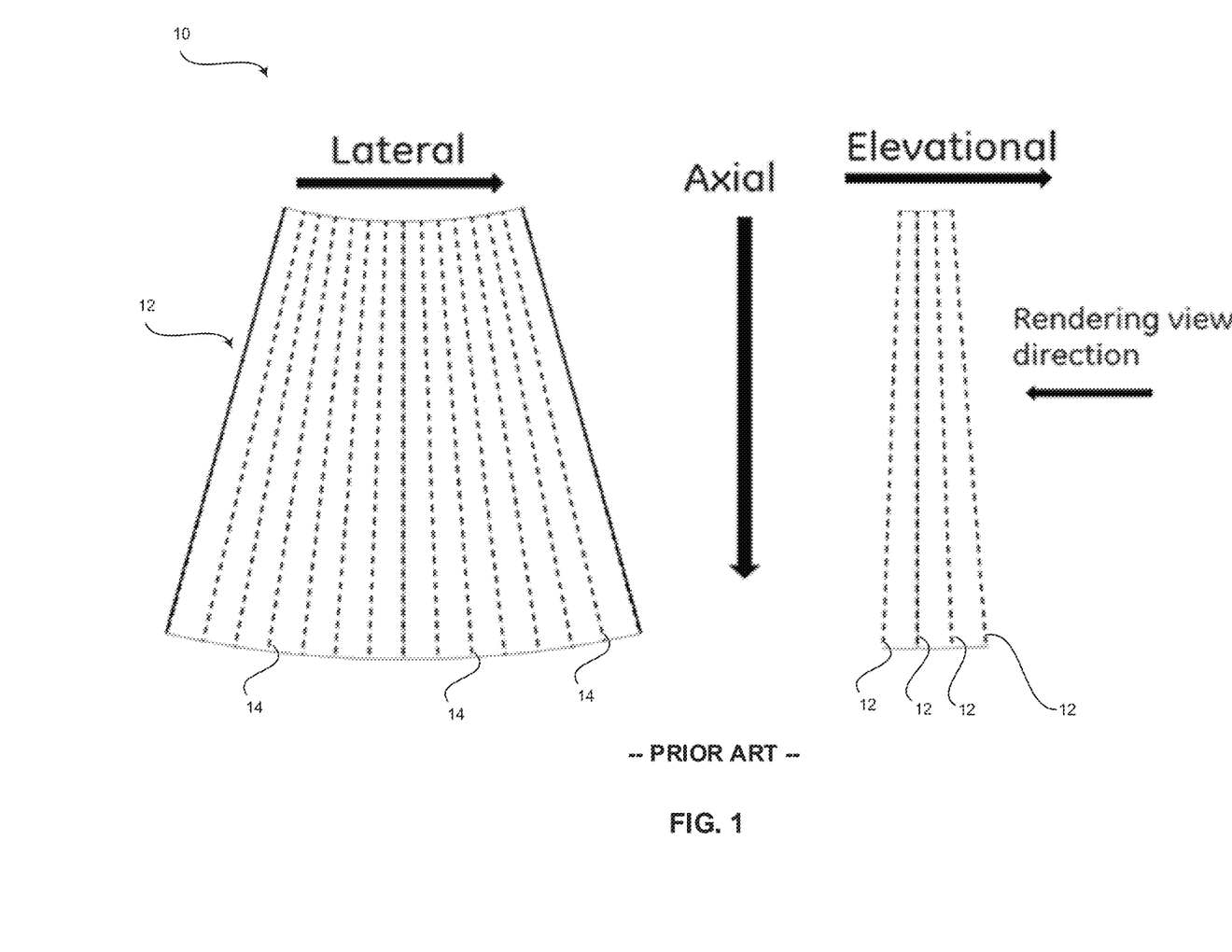
FIG. 1 illustrates an exemplary volume having receive line positions in multiple lateral planes along the elevational direction processed to generate B-mode images used in volume compound imaging (VCI), as known in the art.

Ultrasound volume compound imaging (VCI) involves the acquisition of multiple scan converted B-mode images along an elevational direction and combining the B-mode images using VCI rendering algorithms to generate a volume rendered image. FIG. 1 illustrates an exemplary volume 10 having receive line 14 positions in multiple lateral planes 12 along the elevational direction processed to generate the B-mode images used in VCI, as known in the art. Referring to FIG. 1, each of the lateral planes 12 along an elevational direction includes a plurality of receive lines 14. The receive lines 14 of each lateral plane 12 are laterally aligned causing the partial transparent rendering algorithm to primarily visualize the receive lines 14 of the first lateral plane 12 in the parallel projection rendering view direction.

Figure 2:
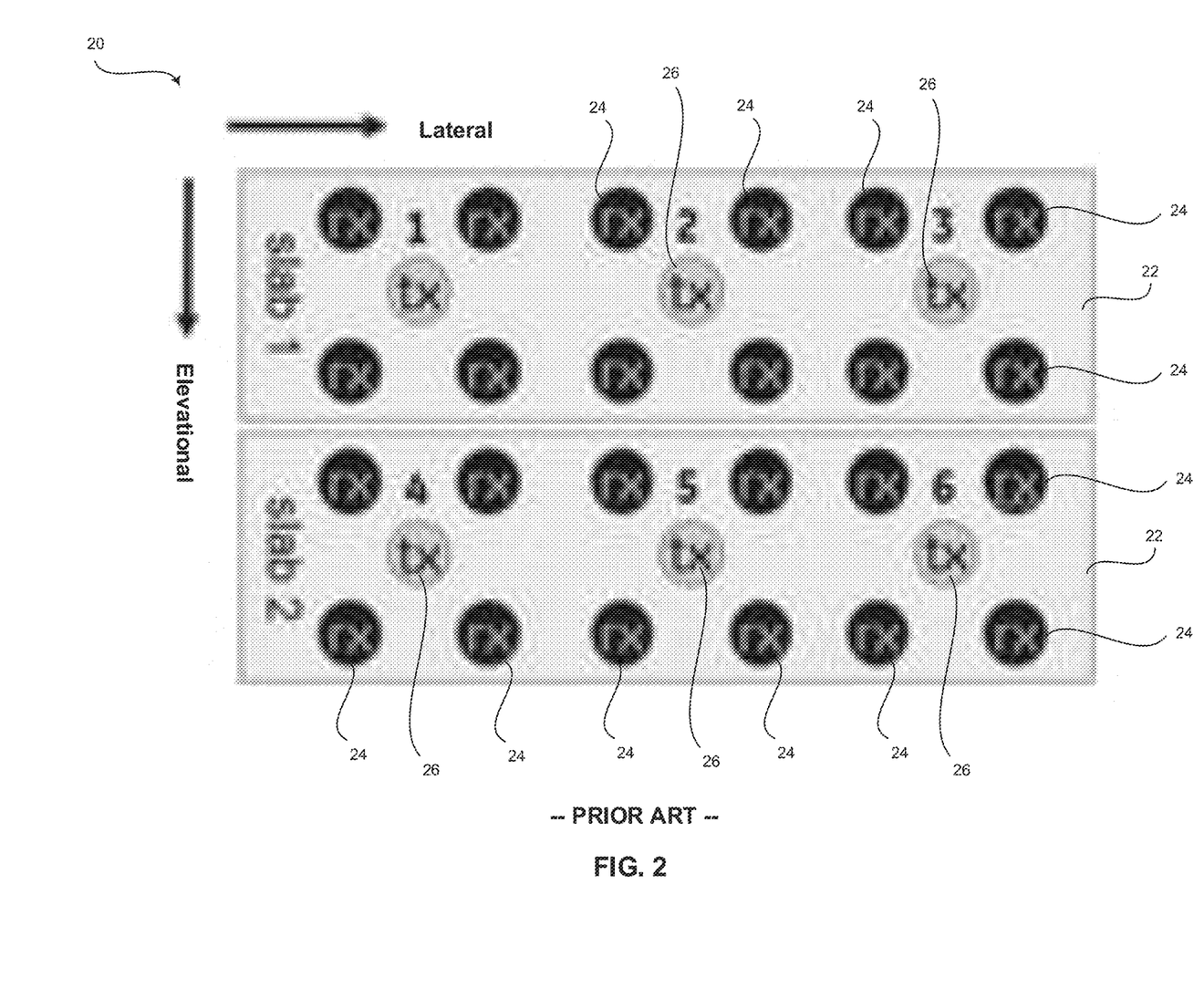
FIG. 2 illustrates exemplary receive line positions in multiple lateral planes along an elevation direction acquired using multi-line acquisition (MLA), as known in the art.

FIG. 2 illustrates exemplary receive line 24 positions in multiple lateral planes 22 along an elevation direction acquired using multi-line acquisition (MLA) 20, as known in the art. Referring to FIG. 2, four (4) receive lines 24 are acquired for each transmit beam 26. As shown in FIG. 2, each of the lateral planes 22 along an elevational direction includes a plurality of receive lines 24. The receive lines 24 of each lateral plane 22 are laterally aligned. Accordingly, similar to FIG. 1, the application of a partial transparent rendering algorithm will primarily visualize the receive lines 24 of the first lateral plane 22 in the parallel projection rendering view direction.

Conventional VCI acquisitions involve a trade-off between frame rates and line densities. For example, line densities are typically increased by increasing the number of lines, which reduces the frame rate. As another example, frame rates are typically increased by decreasing the number of lines, which reduces the line densities.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for increasing effective line density of volume compound ultrasound images while maintaining the frame rate, penetration depth, and other image characteristics, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Certain embodiments may be found in a method and system for providing volume compound images in an A-plane. Various embodiments have the technical effect of increasing effective line density of volume compound ultrasound images while maintaining the frame rate, penetration depth, and other image characteristics.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, MGD, and/or sub-modes of B-mode and/or CF such as Volume Compound Imaging (VCI), Shear Wave Elasticity Imaging (SWEI), TVI, Angio, B-flow, BMI, BMI_Angio, and in some cases also MM, CM, TVD, CW where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 3.

Figure 3:
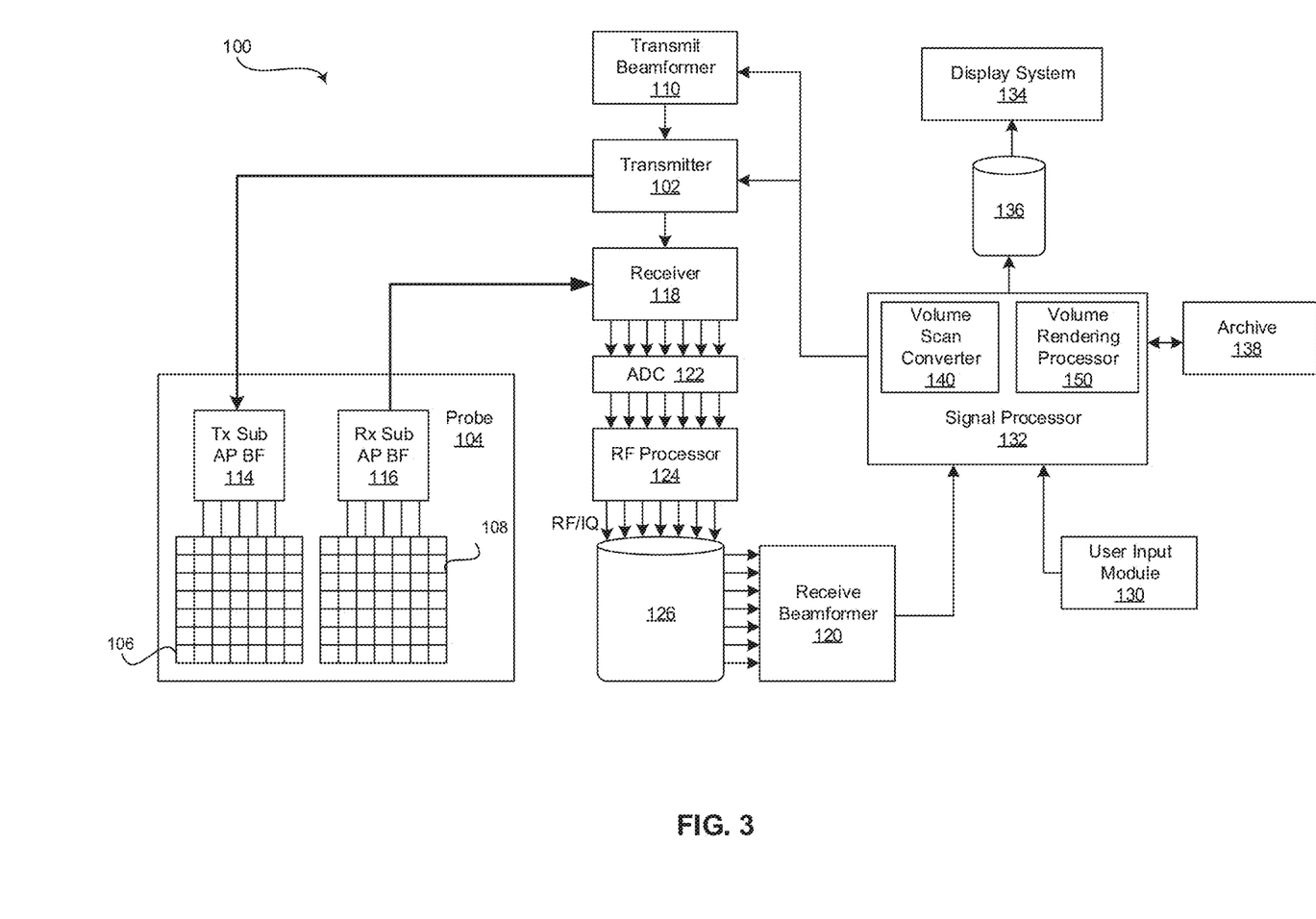
FIG. 3 is a block diagram of an exemplary ultrasound system that is operable to increase effective line density of volume compound ultrasound images while maintaining the frame rate, penetration depth, and other image characteristics, in accordance with various embodiments.

FIG. 3 is a block diagram of an exemplary ultrasound system 100 that is operable to increase effective line density of volume compound ultrasound images while maintaining the frame rate, penetration depth, and other image characteristics, in accordance with various embodiments. Referring to FIG. 3, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements or may be a mechanical one dimensional (1D) array, among other things. The ultrasound probe 104 may comprise a group of transmit transducer elements 106 and a group of receive transducer elements 108, that normally constitute the same elements. In certain embodiments, the ultrasound probe 104 may be operable to acquire ultrasound image data covering at least a substantial portion of an anatomy, such as a heart, a fetus, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, delay and sum the channel signals received from RF processor 124 via the RF/IQ buffer 126 and output beam summed receive lines. In various embodiments, one or more receive beamformers 120 are configured to generate a series of lateral planes that are adjacent in an elevational direction. Each of the lateral planes may include a set of receive lines at a set of lateral positions defined by a delay applied to the received signals by the receive beamformer(s) 120. The delay applied by the receive beamformer(s) 120 may be configured such that at least two sets of lateral positions are alternately applied to generate each set of receive lines. For example, the two sets of lateral positions may include a first set of lateral positions and a second set of lateral positions offset by a one-half (½) pitch line shift. In such an example, the receive beamformer(s) 120 generate a first set of receive lines corresponding with a first lateral plane having a first set of lateral positions and a second set of receive lines corresponding with a second lateral plane having a second set of lateral positions offset by one-half (½) pitch line shift. The delay applied by the receive beamformer(s) 120 to additional planes in the volume may alternate between a first delay corresponding to the first set of lateral positions and the second delay corresponding to the second set of lateral positions. In certain embodiments, different line shift pitches may be applied based at least in part on the delay applied by the receive beamformer(s) 120. For example, one-third (⅓) pitch line shift may be applied to a series of every three (3) lateral planes, one-quarter (¼) pitch line shift may be applied to a series of every four (4) lateral planes, and the like. The resulting processed information may be the beam summed receive lines that are output from the receive beamformer(s) 120 and communicated to the signal processor 132. In accordance with some embodiments, the receiver 118, the plurality of A/D converters 122, the RF processor 124, and the beamformer 120 may be integrated into single beamformer(s), which may be digital. In certain embodiments, the receive beamformer(s) 120 may be multiline ultrasound beamformer(s) configured to produce multiple receive lines in response to each single transmitted beam. The multiline receive beamformer(s) 120 may apply a delay, parallel filtering, and combine the channel signals to produce steered and focused lines according to different sets of lateral positions. In various embodiments, the receive beamformer(s) may be configured to apply Retrospective Transmit Beamforming (RTB) to provide dynamic receive focusing and align the receive lines according to the different sets of lateral positions using time delays computed from a probe geometry used to acquire the ultrasound data.

Figure 4:
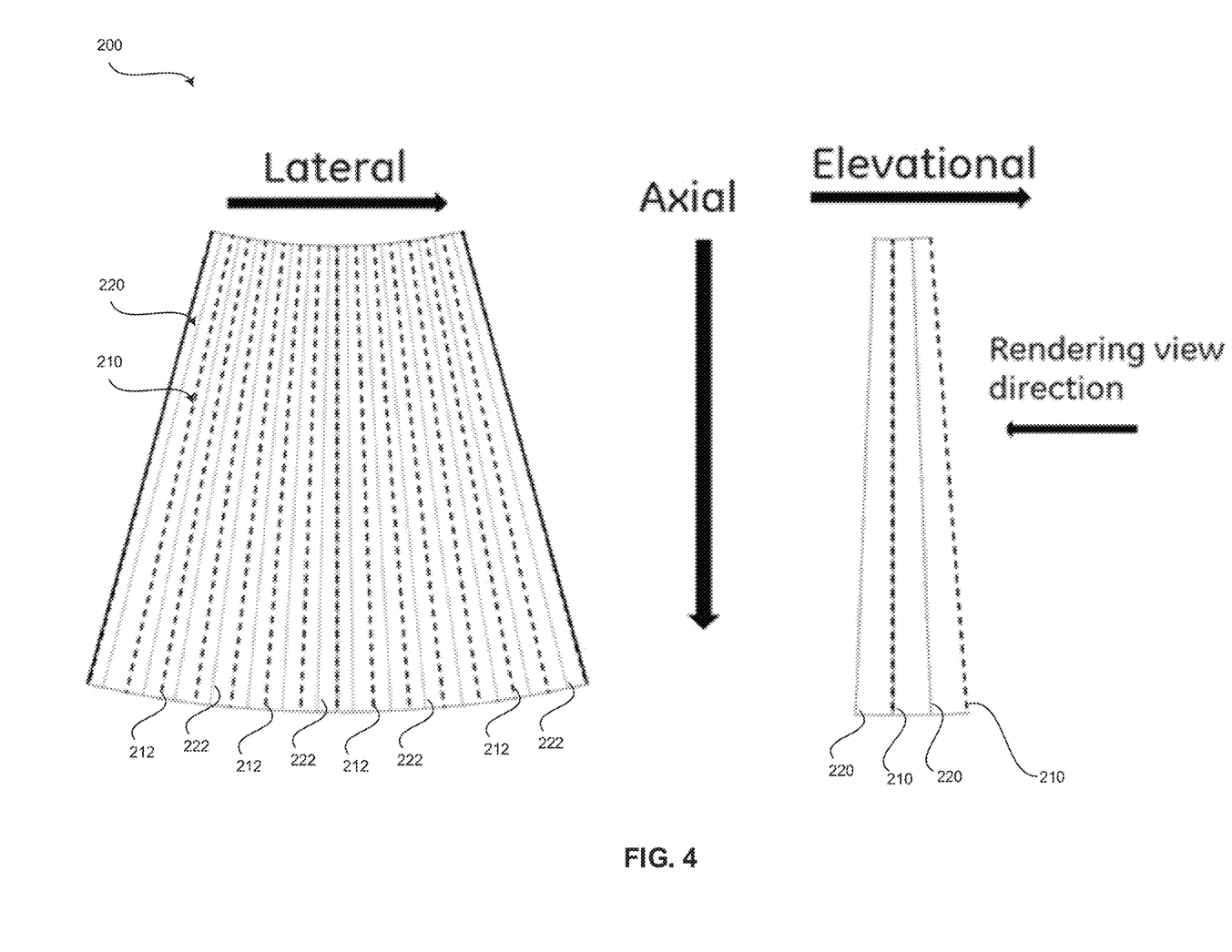
FIG. 4 illustrates an exemplary volume having receive line positions in multiple lateral planes along the elevational direction processed to generate B-mode images used in volume compound imaging (VCI), in accordance with various embodiments.

FIG. 4 illustrates an exemplary volume 200 having receive line positions 212, 222 in multiple lateral planes 210, 220 along the elevational direction processed to generate B-mode images used in volume compound imaging (VCI), in accordance with various embodiments. Referring to FIG. 4, each of the lateral planes 210, 220 along an elevational direction includes a plurality of receive lines 212, 222. The receive lines 212, 222 of alternating lateral planes 210, 220 are laterally offset by one-half (½) pitch line shift providing increased visualization of receive lines 222 in the second lateral plane 220 in the parallel projection rendering view direction to increase the effective line density of a compound image generated from the volume 10 using a partial transparent rendering algorithm.

Figure 5:
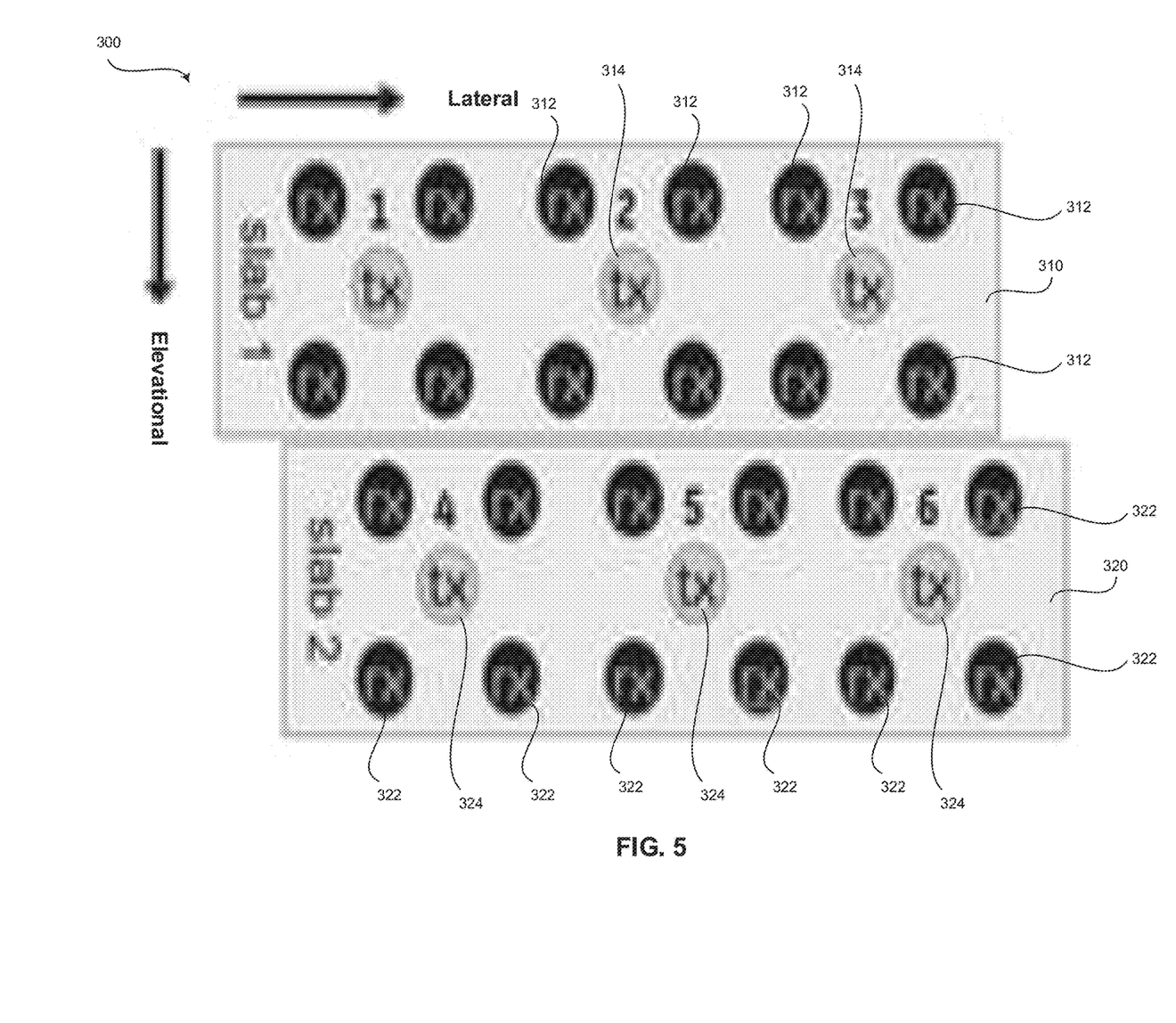
FIG. 5 illustrates exemplary receive line positions in multiple lateral planes along an elevation direction acquired using multi-line acquisition (MLA), in accordance with various embodiments.

FIG. 5 illustrates exemplary receive line positions 312, 322 in multiple lateral planes 310, 320 along an elevation direction acquired using multi-line acquisition (MLA) 300, in accordance with various embodiments. Referring to FIG. 5, four (4) receive lines 312, 322 are acquired for each transmit beam 314, 324. As shown in FIG. 5, each of the lateral planes 310, 320 along an elevational direction includes a plurality of receive lines 312, 322. The receive lines 312, 322 of each lateral plane 310, 320 are laterally offset by one-half (½) pitch line shift providing increased visualization of receive lines 322 in the second lateral plane 320 in the parallel projection rendering view direction to increase the effective line density of a compound image generated using a partial transparent rendering algorithm. Although the transmit beams 324 used to acquire the receive beams 322 in the second lateral plane 320 are shown as offset from the transmit beams 314 used to acquire the receive beams 312 in the first lateral plane 310, unless so claimed, the transmit beams 314, 324 need not be offset and may be aligned in various embodiments. Instead, the receive beamformer(s) 120 may be configured to generate the receive lines 312, 314 at different sets of lateral positions in different lateral planes 310, 320 as described above.

Referring again to FIG. 3, the user input module 130 may be utilized to input patient data, scan parameters, settings, select protocols and/or templates, select an imaging mode, and the like. In an exemplary embodiment, the user input module 130 may be operable to configure, manage and/or control operation of one or more components and/or modules in the ultrasound system 100. In this regard, the user input module 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, the display system 134, and/or the archive 138. The user input module 130 may include button(s), rotary encoder(s), a touchscreen, motion tracking, voice recognition, a mousing device, keyboard, camera and/or any other device capable of receiving a user directive. In certain embodiments, one or more of the user input modules 130 may be integrated into other components, such as the display system 134, for example. As an example, user input module 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform compounding, such as volume compound imaging (VCI), elevation compound imaging (ECI), or the like. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information. In the exemplary embodiment, the signal processor 132 may comprise volume scan converter 140 and a volume rendering processor 150.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/ or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores medical image data, receive line lateral positioning beamforming instructions, and volume rendering processing instructions, for example.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a volume scan converter 140 that comprises suitable logic, circuitry, interfaces and/or code that may be operable to create a data slice from the receive lines 212, 222, 312, 322 of multiple adjacent lateral planes 210, 220, 310, 320 based at least in part on a selected or default slice thickness. For example, in a VCI imaging mode, the slice thickness may be from 1-20 millimeters, which is approximately 2-40 planes at 2-3 planes per millimeter. As another example, in an ECI imaging mode, the slice thickness may be 1 millimeter or less (e.g., 2 planes). The slice thickness may be a default thickness corresponding to the imaging mode selected via the user input module 130. Additionally and/or alternatively, the slice thickness may be selected via the user input module 130. The number of adjacent lateral planes 210, 220, 310, 320 that are obtained to form each data slice may be dependent upon the selected thickness. The created data slice may be provided to the volume rendering processor 150 and/or stored at archive 138 or any suitable data storage medium.

The signal processor 132 may include a volume rendering processor 150 that comprises suitable logic, circuitry, interfaces and/or code that may be operable to receive the data slice from the volume scan converter 140 or archive 138 and perform volume rendering on the data slice. For example, the volume rendering processor 150 may be configured to apply rendering algorithms configured to process the data slice having the lateral planes 210, 220, 310, 320 made up of the laterally offset receive lines 212, 222, 312, 322 by applying weighting to the different lateral planes 210, 220, 310, 320 based on the pitch line shift. In an exemplary embodiment, the rendering algorithms are VCI rendering algorithms. Additionally and/or alternatively, the volume rendering processor 150 may apply ECI or any suitable rendering algorithms based on the selected imaging mode. The volume rendering processor 150 may be configured to generate the compound image in an A-plane. The volume rendering processor 150 may be configured to present the compound image at the display system 134 and/or store the compound image at archive 138 and/or any suitable data storage medium. In certain embodiments, the signal processor 132 may be configured to apply video processing and/or other post-processing to the compound image prior to presentation at the display system 134 and/or storing the compound image at archive 138 and/or any suitable data storage medium.

The display system 134 may be any device capable of communicating visual information to a user. For example, a display system 134 may include a liquid crystal display, a light emitting diode display, and/or any suitable display or displays. The display system 134 can be operable to display information from the signal processor 132 and/or archive 138, such as volume compound images, and/or any suitable information. In various embodiments, the display system 134 is operable to present volume compound images based on B-mode images generated from a plurality of lateral planes 210, 220, 310, 320 along an elevational direction each having a set of receive lines 212, 222, 312, 322 at a set of lateral positions, where the lateral positions of receive lines 212, 222, 312, 322 of adjacent lateral planes 210, 220, 310, 320 are laterally offset by a pitch line shift.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input module 130 may be integrated as a touchscreen display.

Figure 6:
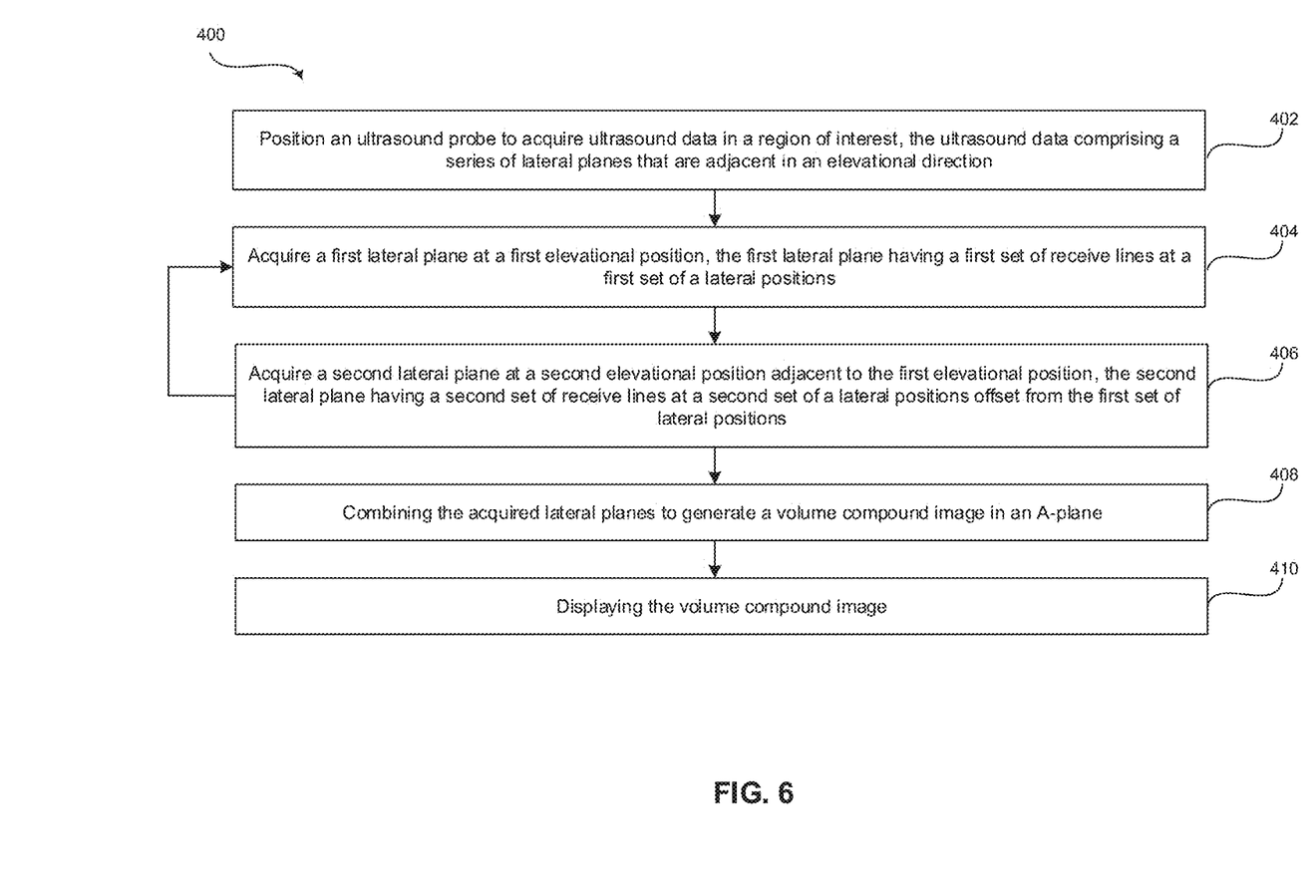
FIG. 6 is a flow chart illustrating exemplary steps for increasing effective line density of volume compound ultrasound images while maintaining the frame rate, penetration depth, and other image characteristics, in accordance with various embodiments.

FIG. 6 is a flow chart 400 illustrating exemplary steps 402-410 for increasing effective line density of volume compound ultrasound images while maintaining the frame rate, penetration depth, and other image characteristics, in accordance with various embodiments. Referring to FIG. 6, there is shown a flow chart 400 comprising exemplary steps 402 through 410. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, an ultrasound probe 104 is positioned to acquire ultrasound data in a region of interest. The ultrasound data includes a series of lateral planes 210, 220, 310, 320 that are adjacent in an elevational direction. For example, a 2D matrix array ultrasound transducer 104 or a 1D array mechanical transducer may be positioned to acquire ultrasound data in a region of interest, such as a fetus, heart, or any suitable anatomical structure.

At step 404, the ultrasound system 100 acquires a first lateral plane 210, 310 at a first elevational position. The first lateral plane 210, 310 includes a first set of receive lines 212, 312 at a first set of lateral positions. For example, receive beamformer(s) 120 may delay and sum channel signals corresponding with echoes received at the ultrasound probe 104 to output the first set of receive lines 212, 312, at the first set of lateral positions. The receive beamformer(s) 120 may be multiline receive beamformer(s) and/or may be configured to apply RTB to provide the focused and steered receive lines 212, 312 at the first set of lateral positions in the first lateral plane 210, 310.

At step 406, the ultrasound system 100 acquires a second lateral plane 220, 320 at a second elevational position adjacent the first elevational position. The second lateral plane 220, 320 includes a second set of receive lines 222, 322 at a second set of lateral positions laterally offset from the first set of lateral positions. For example, the receive beamformer(s) 120 may delay and sum channel signals corresponding with echoes received at the ultrasound probe 104 to output the second set of receive lines 222, 322, at the second set of lateral positions. The delay applied by the receive beamformer(s) 120 to acquire the set of receive lines 222, 322 at the second set of lateral positions may be different than the delay applied at step 404 to acquire the first set of receive lines 212, 312 and the first set of lateral positions such that the second set of lateral positions includes a lateral line shift pitch, such as a pitch of one-half (½), one-third (⅓), one-quarter (¼), or the like. The receive beamformer(s) 120 may be multiline receive beamformer(s) and/or may be configured to apply RTB to provide the focused and steered receive lines 222, 322 at the second set of lateral positions in the second lateral plane 220, 320.

The process may repeat steps 404 and/or 406 until an appropriate number of lateral planes 210, 220, 310, 320 are acquired. For example, the ultrasound system 100 may acquire 2-40 planes. The receive beamformer(s) 120 may be configured to apply a delay corresponding with a default or selected pitch line shift. For example, one-half (½) pitch line shift may be applied to a series of every two (2) lateral planes, one-third (⅓) pitch line shift may be applied to a series of every three (3) lateral planes, one-quarter (¼) pitch line shift may be applied to a series of every four (4) lateral planes, and the like. The resulting processed information may be the beam summed receive lines 212, 222, 312, 322 that are output from the receive beamformer(s) 120 and communicated to the signal processor 132.

At step 408, at least one signal processor 132 of the ultrasound system 100 combines the acquired lateral planes 210, 220, 310, 320 to generate a volume compound image in an A-plane. For example, a volume scan converter 140 of the at least one signal processor 132 may create a data slice from the receive lines 212, 222, 312, 322 of multiple adjacent lateral planes 210, 220, 310, 320 based at least in part on a selected or default slice thickness. The created data slice may be provided to a volume rendering processor 150 of the at least one signal processor 132 to perform volume rendering on the data slice. As an example, the volume rendering processor 150 may be configured to apply rendering algorithms configured to process the data slice having the lateral planes 210, 220, 310, 320 made up of the laterally offset receive lines 212, 222, 312, 322 by applying weighting to the different lateral planes 210, 220, 310, 320 based on the pitch line shift. The rendering algorithms for generating a volume compound image in an A-plane are VCI rendering algorithms.

At step 410, the at least one signal processor 132 of the ultrasound system 100 displays the volume compound image. For example, the volume rendering processor 150 of the at least one signal processor 132 may be configured to present the compound image at the display system 134. In certain embodiments, the signal processor 132 may be configured to apply video processing and/or other post-processing to the compound image prior to presentation at the display system 134. The display system 134 is operable to display the volume compound images based on B-mode images generated from a plurality of lateral planes 210, 220, 310, 320 along an elevational direction each having a set of receive lines 212, 222, 312, 322 at a set of lateral positions, where the lateral positions of receive lines 212, 222, 312, 322 of adjacent lateral planes 210, 220, 310, 320 are laterally offset by a pitch line shift.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for increasing effective line density of volume compound ultrasound images while maintaining the frame rate, penetration depth, and other image characteristics.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
acquiring, by an ultrasound system, a first lateral plane at a first elevational position, the first lateral plane comprising a first set of receive lines at a first set of lateral positions;
acquiring, by an ultrasound system, a second lateral plane at a second elevational position adjacent the first elevational position, the second lateral plane comprising a second set of receive lines at a second set of lateral positions laterally offset from the first set of lateral positions wherein each of the second set of lateral positions are laterally offset from each of the first set of lateral positions by a distance equal to or less than one-third (⅓) the lateral line pitch of the first set of receive lines;

combining, by at least one signal processor, the first lateral plane and the second lateral plane to generate a compound image, wherein no receive lines at the first elevational position overlap with any receive lines at the second elevational position; and presenting, by the at least one processor, the compound image at a display system.

2. The method of claim 1, wherein each of the second set of lateral positions are laterally offset from each of the first set of lateral positions by a distance equal to one-fourth (¼) the lateral line pitch of the first set of receive lines.

3. The method of claim 1, wherein the first set of receive lines at the first set of lateral positions and the second set of receive lines at the second set of lateral positions are generated by at least one multiline receive beamformer.

4. The method of claim 1, wherein the first set of receive lines at the first set of lateral positions and the second set of receive lines at the second set of lateral positions are generated by at least one receive beamformer applying Retrospective Transmit Beamforming (RTB).

5. The method of claim 1, wherein the compound image is a volume compound image in an A-plane generated based at least in part on a volume compound imaging (VCI) rendering algorithm.

6. The method of claim 1, wherein the compound image is an elevation compound image generated based at least in part on an elevation compound imaging (ECI) rendering algorithm.

7. The method of claim 1, wherein:
the first set of receive lines are acquired in response to a first set of transmit beams transmitted at a first set of lateral transmit positions, and
the second set of receive lines are acquired in response to a second set of transmit beams transmitted at a second set of lateral transmit positions laterally offset from the first set of lateral transmit positions.

8. An ultrasound system comprising:
at least one receive beamformer configured to:
acquire a first lateral plane at a first elevational position, the first lateral plane comprising a first set of receive lines at a first set of lateral positions; and
acquire a second lateral plane at a second elevational position adjacent the first elevational position, the second lateral plane comprising a second set of receive lines at a second set of lateral positions laterally offset from the first set of lateral positions wherein each of the second set of lateral positions are laterally offset from each of the first set of lateral positions by a distance equal to or less than one-third (⅓) the lateral line pitch of the first set of receive lines;
at least one signal processor configured to combine the first lateral plane and the second lateral plane to generate a compound image, wherein no receive lines at the first elevational position overlap with any receive lines at the second elevational position; and
a display system configured to present the compound image.

9. The system of claim 8, wherein each of the second set of lateral positions are laterally offset from each of the first set of lateral positions by a distance equal to one-fourth (¼) the lateral line pitch of the first set of receive lines.

10. The system of claim 8, wherein the at least one receive beamformer is at least one multiline receive beamformer.

11. The system of claim 8, wherein the at least one receive beamformer is configured to apply Retrospective Transmit Beamforming (RTB) to acquire the first set of receive lines at the first set of lateral positions and the second set of receive lines at the second set of lateral positions.

12. The system of claim 8, wherein the at least one signal processor is configured to apply a volume compound imaging (VCI) rendering algorithm to generate the compound image, and wherein the compound image is a volume compound image in an A-plane.

13. The system of claim 8, wherein the at least one signal processor is configured to apply an elevation compound imaging (ECI) rendering algorithm to generate the compound image, and wherein the compound image is an elevation compound image.

14. The system of claim 8, wherein the ultrasound system is configured to:
transmit a first set of transmit beams at a first set of lateral transmit positions to acquire the first set of receive lines, and
transmit a second set of transmit beams at a second set of lateral transmit positions laterally offset from the first set of lateral transmit positions to acquire the second set of receive lines.

15. A non-transitory computer readable medium having stored thereon, a computer program having at least one code section, the at least one code section being executable by a machine for causing an ultrasound system to perform steps comprising:
acquiring a first lateral plane at a first elevational position, the first lateral plane comprising a first set of receive lines at a first set of lateral positions;
acquiring a second lateral plane at a second elevational position adjacent the first elevational position, the second lateral plane comprising a second set of receive lines at a second set of lateral positions laterally offset from the first set of lateral positions, wherein each of the second set of lateral positions are laterally offset from each of the first set of lateral positions by a distance equal to or less than one-third (⅓) the lateral line pitch of the first set of receive lines;
combining the first lateral plane and the second lateral plane to generate a compound image, wherein no receive lines at the first elevational position overlap with any receive lines at the second elevational position; and
presenting the compound image at a display system.

16. The non-transitory computer readable medium of claim 15, wherein each of the second set of lateral positions are laterally offset from each of the first set of lateral positions by a distance equal to one-fourth (¼) the lateral line pitch of the first set of receive lines.

17. The non-transitory computer readable medium of claim 15, wherein the first set of receive lines at the first set of lateral positions and the second set of receive lines at the second set of lateral positions are generated by applying Retrospective Transmit Beamforming (RTB).

18. The non-transitory computer readable medium of claim 15, wherein the compound image is a volume compound image in an A-plane generated based at least in part on a volume compound imaging (VCI) rendering algorithm.

19. The non-transitory computer readable medium of claim 15, wherein the compound image is an elevation compound image generated based at least in part on an elevation compound imaging (ECI) rendering algorithm.

\* \* \* \* \*